United States Patent [19]

Missfeldt

[11] Patent Number: 4,808,088
[45] Date of Patent: Feb. 28, 1989

[54] PNEUMATIC DRIVE CIRCUIT FOR AN ARTIFICIAL VENTRICLE INCLUDING SYSTOLIC PRESSURE CONTROL

[75] Inventor: William A. Missfeldt, Ambler, Pa.

[73] Assignee: Temple University of the Commonwealth System of Higher Education, Philadelphia, Pa.

[21] Appl. No.: 911,598

[22] Filed: Sep. 25, 1986

[51] Int. Cl.[4] .............................................. F04B 43/02
[52] U.S. Cl. ...................................... 417/395; 91/443
[58] Field of Search ............................. 91/31, 22, 443; 417/395

[56] References Cited

U.S. PATENT DOCUMENTS

| | | | |
|---|---|---|---|
| 1,484,678 | 2/1924 | Slater | 91/22 |
| 3,541,612 | 11/1970 | Carney | 3/1 |
| 3,869,224 | 3/1975 | Brinkman | 417/395 |
| 4,034,742 | 7/1977 | Thoma | 128/1 D |
| 4,158,530 | 6/1979 | Bernstein | 417/389 |
| 4,402,254 | 9/1983 | Petrimanx et al. | 91/31 X |
| 4,548,550 | 10/1985 | Tsuji | 417/394 X |

Primary Examiner—Carlton R. Croyle
Assistant Examiner—Eugene L. Szczecina, Jr.
Attorney, Agent, or Firm—Seidel. Gonda, Lavorgna & Monaco

[57] ABSTRACT

A pneumatic drive circuit for a pneumatically-driven artificial ventricle having a gas chamber and a blood chamber separated by a flexible diaphragm. The drive circuit comprises a source of pressurized gas at a preselected pressure. Valves operatively associated with the gas chamber of the ventricle admit gas to the gas chamber during systole and exhaust gas from the gas chamber during diastole. The drive circuit includes pneumatic logic circuitry for actuating the valves. The logic circuitry includes circuitry for causing the valves to admit gas to the gas chamber during systole at a pressure which increases gradually from zero pressure to a pressure less than the preselected pressure, and then increases rapidly to the preselected pressure.

7 Claims, 2 Drawing Sheets

PNEUMATIC DRIVE CIRCUIT FOR AN ARTIFICIAL VENTRICLE INCLUDING SYSTOLIC PRESSURE CONTROL

FIELD OF THE INVENTION

The present invention relates to artificial hearts, and in particular a pneumatic drive circuit for a pneumatically driven artificial ventricle.

BACKGROUND OF THE INVENTION

In recent years, there have been total artificial hearts under development utilizing a wide variety of physical principles. Some of the artificial hearts utilize a Stirling engine, others use an electric torque motor with a pusher plate, others an electrical solenoid-driven pusher plate, others a pneumatically-powered sac, and still others an electric motor roller screw and cam.

One type of artificial heart under development is similar in principle to the well-known Jarvik 7 artificial heart, which has an artificial heart ventricle comprising a blood chamber and a gas chamber separated by a flexible diaphragm. The diaphragm is caused to flex by air alternately admitted to and exhausted from the air chamber.

This type of artificial heart must be powered wtih an "air driver." The standard device for driving the artificial heart accepts compressed air from a storage reservoir and manipulates it to provide a continuous series of air pressure pulses to each ventricle. The design of the conventional "air driver" permits independent control of the pressure intensity to the left and right ventricles. Also controllable is the duration of the pressure pulse (systole) and the time during pressure venting (diastole), both of which, taken together, determine the beats-per-minute.

The conventional "air driver" is not without its disadvantages. It is expensive, large and heavy, restricting a patient's degree of freedom and mobility. In addition, the conventional "air driver" requires electrical power for many of its operating elements. Thus, the conventional "air driver" is susceptible to electrical noise and interference, and must be shielded from water and combustible gases.

It is an object of the present invention to provide a fully-pneumatic drive circuit for an artificial heart of the type having a gas chamber and a blood chamber separated by a flexible diaphragm which is smaller, lighter and thus would provide a patient with a somewhat greater of degree of freedom and mobility than known heart drivers.

It is also an object of the invention to reduce the cost and complexity of the driver while maintaining performance and reliability by utilizing off-the-shelf, proven pneumatic digital logic elements.

The pneumatic drive circuit of the present invention requires no electrical components and therefore eliminates the need for electric power. This makes the circuit immune to power line noise and static electricity. Immersion in water does not effect it. And, since because it is pneumatic it cannot generate sparks, it is safe to operate in the presence of combustible vapors or gases.

SUMMARY OF THE INVENTION

The present invention is a pneumatic drive circuit for a pneumatically-driven artificial ventricle having a gas chamber and a blood chamber separated by a flexible diaphragm. The drive circuit comprises a source of gas at a preselected pressure, valve means operatively associated with the gas chamber for admitting said gas to the gas chamber during systole and exhausting said gas from the gas chamber during diastole. The drive circuit further includes pneumatic logic circuitry for actuating the valve means, the logic circuitry including means for causing the valve means to admit the gas to the gas chamber during systole at a pressure which increases gradually from zero pressure to a pressure less than the preselected pressure, and then rapidly to the preselected pressure.

An important, but by no means the only, feature of the pneumatic drive circuit of the present invention is that the gradual increase in gas pressure during systole results in a much gentler closure of the blood inflow valve (the mitral valve) on the blood side of the artificial ventricle, leading to longer valve life. This feature is not available in known heart drivers.

DESCRIPTION OF THE DRAWINGS

For the purpose of illustrating the invention, there is shown in the drawings a form which is presently preferred; it being understood, however, that this invention is not limited to the precise arrangement and instrumentalities shown.

DESCRIPTION OF THE INVENTION

Figure 1:
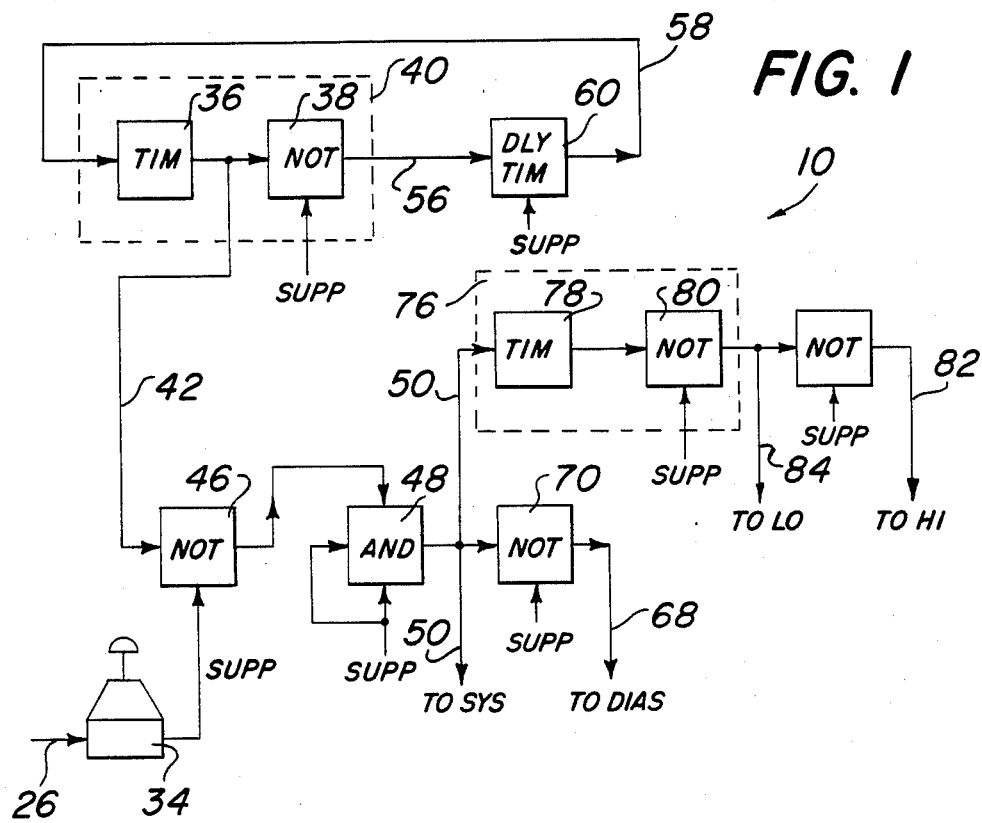
FIG. 1 is a schematic diagram of the pneumatic drive circuit according to the present invention.

Referring now to the drawings, wherein like numerals indicate like elements, there is shown in FIG. 1 a pneumatic drive circuit 10 in accordance with the present invention. Circuit 10 comprises various conventional, off the-shelf pneumatic logic elements which utilize the compressed gas, typically air, already present for driving the artificial heart, to generate the timing and air pressure pulses required by the artificial heart. Since all of the logic elements in FIG. 1 are conventional, they need not be explained or described here in detail. Instead, each of the logic elements will be discussed in connection with the description of the operation of the circuit of Figure 1 herein below. The pneumatic logic elements provide the same accurate timing as electronic digital logic, but they do not require electric current for their operation. Instead, they can be powered by the same air source already present to power the pneumatic ventricles.

In addition, because the internal components of the logic elements have no frictional motion, they are extremely durable and can operate for many millions of cycles without failure.

Figure 2:
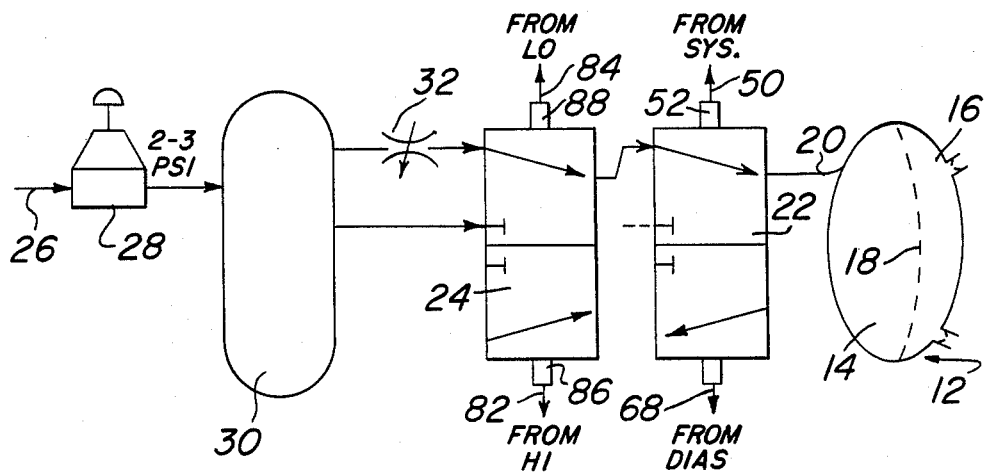
FIG. 2 illustrates the operating components, including the valves and artificial ventricle, of the drive circuit of the present invention.

FIG. 2 illustrates the operating elements of the pneumatic drive circuit of the present invention. The artificial ventricle to be driven is generally designated by reference numeral 12, and comprises a gas chamber 14 and a blood chamber 16 separated by a flexible diaphragm 18. Gas, typically air, is admitted to and exhausted from gas chamber 14 through a conduit 20 which is supplied from a pair of pilot valves 22 and 24. Pilot valves 22 and 24 are operated by pneumatic control signals generated by the drive circuit of FIG. 1, as will be described more fully hereinbelow. Pilot valves 22 and 24 are otherwise conventional.

Operating gas, preferably at 2 to 3 psi, is supplied to pilot valves 22 and 24 from a source 26 via regulator 28 and surge tank 30. Source 26 may be a small, portable compressor (not shown). A needle valve 32 or other restriction is provided between surge tank 30 and pilot valve 24 to cause a substantial pressure drop, which gives a very gradual pressure rise in chamber 14 for about 50 ms, to allow the inflow valve to blood chamber 16 to close gently. A needle valve is preferred, since it allows the slope of pressure rise and rise time to be controlled. Suitable pressure sensors, not shown, may be provided in the air supply lines to monitor air pressure.

Operation of the circuit of the present invention will now be described with reference to FIGS. 1, 2 and 3.

Supply gas for the logic elements of the circuit of FIG. 1 may be derived from the same source 26 of pressurized gas which operates pilot valves 22 and 24. Supply pressure is regulated by a regulator 34, and the regulated gas is supplied to the "SUPP" inputs of the logic elements of FIG. 1. A preferred, but by no means the only, supply pressure is 10 psi, adjusted by a regulator 34, so that only a single source 26 at 15 psi or more is required to operate both the logic circuitry in FIG. 1 and the operating elements in FIG. 2.

Timer 36 and NOT element 38 together comprise a first pulse timer 40. Supply gas admitted to NOT element 38 causes pressure in line 42 to build very gradually, as shown in the first waveform in FIG. 3. The pressure increases gradually very similar to the electrical analogy of a voltage on a capacitor being charged through a resistor. When the pressure in line 42 reaches point 44 on the waveform in FIG. 3, NOT element 46, which operates as a comparator, will be actuated, and its output will drop to zero. This, in turn, causes the output of AND element 48 to drop to zero. This signals the end of systole, and, therefore, the start of diastole. The output of AND element 48 is connected by line 50 to pilot input 52 on pilot valve 22. This causes pilot valve 22 to change state from admitting gas into chamber 14 to exhausting gas from chamber 14. The pressure waveform of line 50 is shown as the fourth waveform in FIG. 3.

Even after the start of diastole, the pressure in line 42 continues to rise. When that pressure reaches point 54 on the waveform in FIG. 3, NOT element 38 is actuated, and the pressure in output line 56 is internally vented to zero, allowing the pressure in line 42 to decay to zero. When the pressure in line 56, which is shown as the second waveform in FIG. 3, is vented to zero, the pressure in feedback line 58 is also vented to zero by delay timer 60, at the same time. The pressure waveform for feedback line 58 is shown as the third waveform in FIG. 3.

As noted, the pressure in feedback line 58 forms the input to timer 36. After a predetermined time, the pressure in output line 56 will increase, as shown at point 62 on the waveform in FIG. 3. After a short delay, preferably approximately 50 ms, provided by delay timer 60 (in order to permit the pressure in line 42 to decay sufficiently to reset NOT element 46), pressure in feedback line 58 is reapplied, as shown at point 64 on the waveform in FIG. 3.

Figure 3:
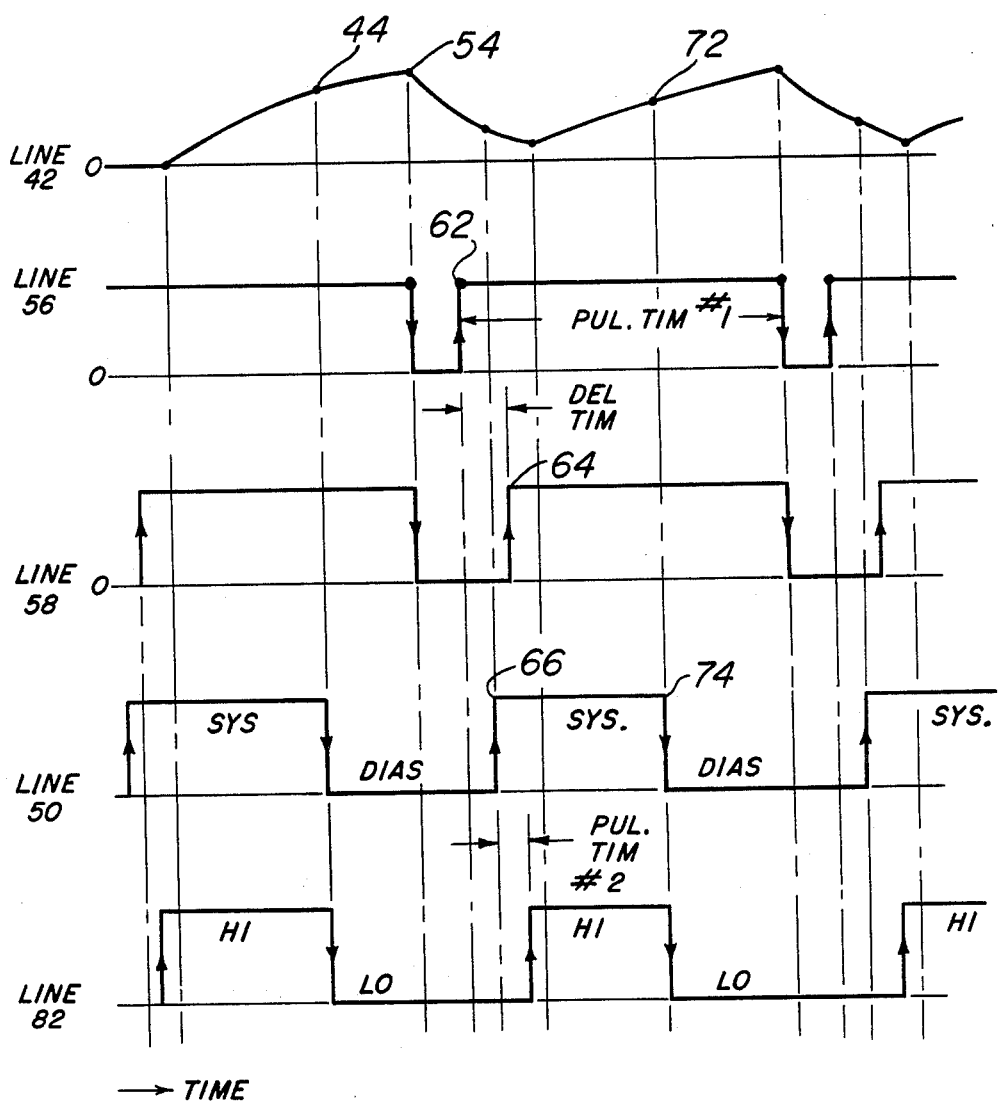
FIG. 3 is a timing diagram, showing the pressure waveforms at key points of the operating cycle of the pneumatic drive circuit of the present invention.

As the pressure in line 42 decays sufficiently, NOT element 46 is reset, providing an output to AND element 48, which results in a pressure in line 50, indicated as point 66 on the waveform of FIG. 3. This begins the next systole cycle.

The systole signal pressure 50 is applied to pilot valve 22 while the diastole pressure signal 68 is vented by NOT element 70. When these occur, pilot valve 22 shifts, and air pressure is admitted to chamber 14, pushing on the diaphragm, thus expelling blood from blood chamber 16. When the pressure in line 42 reaches point 72 on the waveform of FIG. 3, systole ends, diastole begins, as indicated at point 74 on the waveforms of FIG. 3, and the cycle repeats.

The pressure rise in the ventricle at the very start of systole is shaped to a more gradual increase by a second pulse timer 76 made up of timer element 78 and NOT element 80. As seen in FIG. 1, output line 50 to pilot valve 22 is also connected to second pulse timer 76. When the pressure in output line 50 increases, signaling the start of systole, that pressure signal is delayed by timer 78 and, after a predetermined delay, appears as a pressure on output line 82 and a zero pressure on output line 84. Output lines 82 and 84 are the input signals for pilot inputs 86 and 88, respectively, on pilot valve 24. Once timer 76 times out, the pressure signals on output lines 82 and 84 cause pilot valve 24 to shift, admitting the full pressure of the surge tank to gas chamber 14. By delaying the time pilot valve 24 shifts, a much more gradual pressure rise at the very start of systole is obtained. This results in a much gentler closure of the blood inflow valve in blood chamber 16, promoting longer valve life.

It will be appreciated that the foregoing invention completely eliminates the need for electrical power to produce the required air pressure pulses. It is therefore less vulnerable to accidental shutdown due to power lines outages or transients, and is also simpler and, therefore, more reliable. The invention also provides a more gradual increase in pressure at the very start of systole, promoting longer valve life for the blood inflow valve.

The present invention may be embodied in other specific forms without departing from the spirit or essential attributes thereof and, accordingly, reference should be made to the appended claims, rather than to the foregoing specification, as indicating the scope of the invention.

I claim:

1. A pneumatic drive circuit for a pneumatically-driven artificial ventricle having a gas chamber and a blood chamber separated by a flexible diaphragm, comprising
(a) a single source of gas at a preselected positive pressure,
(b) valve means operatively associated with the gas chamber for controllably admitting gas from the source to the gas chamber through a restriction at the beginning of systole and admitting gas from the source directly to the gas chamber during the remainder of systole and exhausting said gas from the gas chamber during diastole, and
(c) pneumatic logic circuitry for actuating said valve means, said logic circuitry including means for causing the valve means to controllably admit said gas to the gas chamber during systole at a pressure which increases gradually at the beginning of systole from zero pressure to a pressure less than the preselected pressure and then increases rapidly to the preselected pressure.

2. A pneumatic drive circuit according to claim 1, wherein the means for causing the valve means to controllably admit gas at a gradually increasing pressure comprises a pneumatic timer circuit.

3. A pneumatic drive circuit according to claim 2, wherein the timer circuit is arranged to delay the admission of gas directly to the gas chamber for a preselected time after the start of systole.

4. A pneumatic drive circuit according to claim 1, wherein the pneumatic logic circuit is supplied by the same source of gas as the artificial ventricle.

5. A pneumatic drive circuit according to claim 1, wherein the valve comprises first and second pilot valves in series between the source of gas and the gas chamber and actuated by control signals from the pneumatic logic circuit.

6. A pneumatic drive circuit for a pneumatically-driven artificial ventricle having a gas chamber and a blood chamber separated by a flexible diaphragm, comprising
 (a) a single source of gas at a preselected positive pressure,
 (b) means for regulating said preselected pressure,
 (c) valve means for selectably controlling the flow of gas from the source to the gas chamber of the ventricle through a restriction at the beginning of systole and directly from the source to the gas chamber during the remainder of systole and from the gas chamber to atmosphere during diastole,
 (d) pneumatic logic circuitry supplied by said source of gas for actuating said valve means, said logic circuitry including
  (i) means for generating control signals to said valve means representing the start of systole and the start of diastole, and
  (ii) timing means for generating a delayed signal to the valve means a preselected time after the start of systole for causing the valve means to controllably admit said gas to the gas chamber during systole at a pressure which increases gradually at the beginning of systole from zero pressure to a pressure less than the preselected pressure, and then increases rapidly to the preselected pressure.

7. A pneumatic drive circuit according to claim 6, wherein the valve means comprises first and second pilot valves in series between the source of gas and the gas chamber.

* * * * *